United States Patent [19]

Perez-Soler et al.

[11] Patent Number: 5,384,127
[45] Date of Patent: * Jan. 24, 1995

[54] STABLE LIPOSOMAL FORMULATIONS OF LIPOPHILIC PLATINUM COMPOUNDS

[75] Inventors: Roman Perez-Soler; Insook Han; Abdul R. Khokhar, all of Houston, Tex.

[73] Assignee: Board of Regents, The University of Texas System, Austin, Tex.

[*] Notice: The portion of the term of this patent subsequent to Aug. 20, 2008, has been disclaimed.

[21] Appl. No.: 998,413

[22] Filed: Dec. 29, 1992

Related U.S. Application Data

[60] Continuation-in-part of Ser. No. 709,121, May 31, 1991, Pat. No. 5,186,940, which is a division of Ser. No. 914,591, Oct. 7, 1986, Pat. No. 5,041,581, which is a continuation-in-part of Ser. No. 788,750, Oct. 18, 1985, abandoned.

[51] Int. Cl.$^6$ .................. A61K 37/22; A61K 31/28; C07F 15/00
[52] U.S. Cl. .................. 424/450; 514/492; 556/137
[58] Field of Search .................. 556/137; 424/450; 514/492

[56] References Cited

U.S. PATENT DOCUMENTS

| | | | |
|---|---|---|---|
| 3,904,663 | 9/1975 | Tobe et al. | 260/429 R |
| 3,993,754 | 11/1976 | Rahman et al. | 424/177 |
| 4,115,418 | 10/1978 | Gale et al. | 260/429 R |
| 4,137,248 | 1/1979 | Gale et al. | 260/429 R |
| 4,140,707 | 2/1979 | Cleare et al. | 260/429 R |
| 4,169,846 | 10/1979 | Kidani et al. | 260/429 R |
| 4,203,912 | 5/1980 | Hydes et al. | 260/429 R |
| 4,225,529 | 9/1980 | Hydes et al. | 260/429 R |
| 4,230,631 | 10/1980 | Hydes et al. | 260/429 R |
| 4,235,871 | 11/1980 | Papahadjoponlous | 424/19 |
| 4,241,046 | 12/1980 | Papahadjoponlous | 424/19 |
| 4,256,652 | 3/1981 | Kidani et al. | 260/429 R |
| 4,271,085 | 6/1981 | Amundsen et al. | 260/429 R |
| 4,284,579 | 8/1981 | Meischen et al. | 260/429 R |
| 4,330,534 | 5/1982 | Sakurai et al. | 424/182 |
| 4,431,666 | 2/1984 | Bulten et al. | 424/287 |
| 4,466,924 | 8/1984 | Verbeek et al. | 260/429 R |
| 4,522,803 | 6/1985 | Lenk et al. | 424/1.1 |
| 4,657,927 | 4/1987 | Cleare et al. | 514/492 |
| 4,661,516 | 4/1987 | Brown et al. | 514/492 |
| 4,663,167 | 5/1987 | Lopez-Berestein | 514/37 |
| 4,680,308 | 7/1987 | Schwartz et al. | 514/492 |
| 4,760,155 | 7/1988 | Heffernan et al. | 556/136 |
| 4,760,156 | 7/1988 | Heffernan et al. | 556/136 |
| 4,760,157 | 7/1988 | Child et al. | 556/137 |
| 4,946,954 | 8/1990 | Talebian et al. | 536/121 |
| 4,956,459 | 8/1990 | Talebian et al. | 536/121 |
| 5,041,581 | 8/1991 | Khokhar et al. | 556/137 |
| 5,117,022 | 5/1992 | Khokhar et al. | 556/137 |
| 5,178,876 | 1/1993 | Khokhar et al. | 424/450 |

FOREIGN PATENT DOCUMENTS

| | | |
|---|---|---|
| 569425 | 6/1986 | Australia . |
| 0113508 | 7/1984 | European Pat. Off. . |
| 0130482 | 1/1985 | European Pat. Off. . |
| 0136012 | 4/1985 | European Pat. Off. . |
| 0193936 | 9/1986 | European Pat. Off. . |
| 0198765 | 10/1986 | European Pat. Off. . |
| 0237450 | 9/1987 | European Pat. Off. . |
| 2160867 | 1/1986 | United Kingdom . |
| WO86/01102 | 2/1986 | WIPO . |
| WO88/03925 | 6/1988 | WIPO . |

OTHER PUBLICATIONS

Chemical Abstract, "Cis-1,2-Diaminocyclohexane Platinum Complexes", 101:177510w (1984).
Maeda, Japan Journal Cancer Research (Gann), "Liposoluble Platinum(II) Complexes with Antitumor Activity", 77:523–525 (Jun. 1986).
Kihara, Chemical Abstracts, "Organoplatinum Complexes as Antineoplastics", 105:134160x (1986).
Craciunescu, et al., "On the Preparation, Antitumour (List continued on next page.)

Primary Examiner—José G. Dees
Assistant Examiner—Porfirio Nazario
Attorney, Agent, or Firm—Arnold, White & Durkee

[57] ABSTRACT

Lipophilic complexes having the structure

DACH—Pt—R$_2$ where DACH is diaminocyclohexane, and where R is a linear alkyl carboxylato group having from about 5 to about 18 carbon atoms, have desirable stability when entrapped within lipid bilayers, and exhibit high entrapment efficiency and in vivo antitumor activity.

11 Claims, No Drawings

OTHER PUBLICATIONS and Cytotoxic Evaluation of Some New Analogues of the Cis-Dichloro(1,2-Diamino-Cyclohexane) Platinum(II) Complex", Eur. J. Med. Chem., 19:353-357 (1984).

Sur, et al., "Effect of Liposomal Encapsulation of Cis-Platinum Diamminodichloride in the Treatment of Ehrlich Ascites Carcinoma", Oncology, 40:372-376 (1983).

Freise, et al., "Pharmacokinetics of Liposome Encapsulated Cisplatin in Rats", Archives Internationales de Pharmacodynamie et de Therapie, 258:180-192 (Aug. 1982).

Kaledin, et al., "Intralymphatic Administration of Liposome-Encapsulated Drugs to Mice: Possibility for Suppression of the Growth of Tumor Metastases in the Lymph Nodes", JNCI, 66:881-886 (May 1981).

Deliconstantinos, et al., "Dichlorobiscyclopentylamine-platinum(II) into Liposomes Enhances its Uptake by ADJ/PC6A Tumors Implanted Subcutaneously Into Mice", Biochem. Soc. Trans., 5:1326-1328 (1977).

Yatvin, et al., "Selective Delivery by Hyperthermia of Liposome Encapsulated Cis Dichlorodiamine Platinum(II) and Tumor Growth Delay (Meeting Abstract)", Proc. Am. Assoc. Cancer Res., 21:281 (1980).

Szoka, Jr., and Papahadjopoulos, "Comparative Properties and Methods of Preparation of Lipid Vesicles (Liposomes)", Ann. Rev. Biophys. Bioeng., 9:467-508 (1980).

Swartz, "Preparation and Antitumor Evaluation of Water-Soluble Derivates of Dichloro(1,2-Diaminocyclohexane)Platinum(II)", Chemical Abstracts, 88:16014k (1978).

Swartz et al., "Preparation and Antitumor Evaluation of Water-Soluble Derivatives of Dichloro(1,2-Diaminocyclohexane)Platinum(II)[1,2]", Cancer Treatment Reports, 61:1519-1525 (Nov. 1977).

Perez-Soler, "Toxicity and Antitumor Activity of cis-Bis-cyclopentenecarboxylato-1,2-diaminocyclohexane Platinum(II) Encapsulated in Multi-lamellar Vesicles", Cancer Research 46, 6269-6273 (1986).

Connors, "New Platinum Complexes with Anti-Tumor Activity", Chem. Biol. Interactions, 5:415-424 (1972).

Ridgway et al., "Analogs of Sulfato 1,2-Diaminocyclohexane Platinum(II). I. Modifications in Leaving Ligand", J. Clin. Hematol. Oncol. 7:220-229 (1977).

Burchenal, "Rationale of Combination Chemotherapy", Chemical Abstracts 93:125661t (1980).

Appleton, "Reactions of Platinum(II) Aqua Complexes", Chemical Abstracts 101:182656c (1984).

Speer, "Malonato-1,2-Diaminocyclohexaneplatinum-(II), A Potential Antitumor Agent", Chemical Abstracts 84:5403n (1976).

Khokhar, "The Synthesis and Antitumor Properties of a Series of Water Soluble Carboxylato(1,2-diaminocyclohexane)platinum(II) Complexes", Chemical Abstracts 103:226308p (1980).

Tzu, "Synthesis and Study of Some Platinum Complexes with Dicarboxylic Acids", Chemical Abstracts 94:218774t (1981).

Khokhar et al., "The Synthesis and Antitumor Properties of a Series of Water Soluble Carboxylato-(1,2-Diaminocyclohexane)Platinum(II) Complexes", Inorganica Chimica Acta, 108:63-66 (1985).

Perez-Soler et al., "Phase I Clinical and Pharmacological Study of Liposome-entrapped cis-Bis-neodecanoato-trans-R,R-1,2-diaminocyclohexane Platinum(II)", Cancer Research, 50:4254-4259 (Jul. 15, 1990).

Khokhar et al., "Toxicity and Antitumor Activity of cis-bis-carboxylato-(trans-R,R-1,2-diaminocyclohexane) Platinum(II) Complexes Entrapped in Liposomes", Cancer, Chemotherapy and Pharmacology, 23(4):219-224 (1989).

STABLE LIPOSOMAL FORMULATIONS OF LIPOPHILIC PLATINUM COMPOUNDS

The U.S. government has certain rights in this invention pursuant to National Institutes of Health grant no. CA 45423.

This patent application is a continuation in part of U.S. Ser. No. 709,121, filed on May 31, 1991, now issued as U.S. Pat. No. 5,186,940, which was a divisional of U.S. Ser. No. 914,591, filed on Oct. 7, 1986, now issued as U.S. Pat. No. 5,041,581, which was a continuation in part of U.S. Ser. No. 788,750, filed on Oct. 18, 1985, now abandoned. These patent applications are incorporated here by reference.

BACKGROUND OF THE INVENTION

The present invention relates to platinum based drugs and methods of using such drugs and formulations thereof in antitumor therapy.

Some platinum based drugs are known to have useful antitumor activity. However, such drugs are also known to have various problems, such as toxicity or unsuitability for practical formulation and administration to patients. For example, cisplatin is one such drug with a significant level of antitumor activity, but which also exhibits significant nephrotoxicity and neurotoxicity.

Some of the present inventors previously developed certain lipophilic cisplatin analogs which can be entrapped in liposomes and which have the general structure:

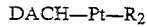

where DACH is diaminocyclohexane, and where R is a branched aliphatic carboxylato group of 5–10 carbons. One of the these complexes, cis-bis-neodecanoato-trans-R,R-1,2-diaminocyclohexane platinum-(II), entrapped in multilamellar vesicles composed of dimyristoyl phosphatidyl choline (DMPC) and dimyristoyl phosphatidyl glycerol (DMPG) at a 7:3 molar ratio (L-NDDP), has been the subject of a Phase I study in humans, and is now in two other clinical studies. Although information on the antitumor activity of L-NDDP in humans is not yet available due to its early stage of development, all preclinical information to date suggests that the concept of a lipophilic cisplatin analog entrapped in liposomes may be a therapeutic strategy of substantial use in the treatment of certain human malignancies.

However, L-NDDP has two major limitations. First, NDDP is a mixture of 15 to 20 isomers, thus making its full chemical characterization difficult, if not impossible. The second shortcoming relates to stability. NDDP undergoes chemical degradation into one or more active intermediates while entrapped in liposomes. The chemical degradation is essential for the complex to exert its antitumor activity in vivo, and is highly dependent on the presence and the relative amount of the phospholipid DMPG within the lipid bilayers. In other words, when liposomes devoid of DMPG are used, NDDP does not undergo degradation within the lipid bilayers and its in vivo antitumor activity is markedly reduced. But because of this degradation, L-NDDP does not meet standard chemical stability criteria for a pharmaceutical product.

Therefore, a need exists for improved formulations which will retain desirable antitumor activity while having improved chemical stability.

SUMMARY OF THE INVENTION

The present invention relates to liposomal formulations of lipophilic platinum complexes having the structure

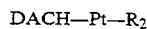

where DACH is diaminocyclohexane, and where R is a linear alkyl carboxylato group having from about 5 to about 18 carbon atoms. The number of carbon atoms is preferably 5–12, most preferably 5–6. The two R groups are preferably the same, but do not necessarily have to be the same.

The platinum complexes of the present invention are preferably formulated in liposomes, lipid vesicles comprising one or more phospholipids which encapsulate or entrap the platinum complex. The preferred phospholipids for use in the present invention are dimyristoyl phosphatidyl choline and dimyristoyl phosphatidyl glycerol, but others could be used. The liposomes are preferably multilamellar, but can also be unilamellar or have an undefined lamellar construction.

The present invention also relates to methods of inhibiting tumor growth which comprise administering to a mammal an amount effective to inhibit tumor growth of a complex as described above.

Complexes with a leaving group (R) of 5 or 6 carbons are completely stable when entrapped within lipid bilayers, whether or not DMPG is present. They also have a very high entrapment efficiency (% drug initially added that becomes associated with the lipid vesicles), usually greater than 90%, exhibit in vivo antitumor activity similar to or greater than that of cisplatin in murine leukemias sensitive to cisplatin, and have also significant in vivo antitumor activity in murine leukemias resistant to cisplatin. Complexes where the R group has 7–12 carbons are very stable ($\geq 95\%$ at 6 hours) in liposomes comprising DMPC:DMPG at a 7:3 molar ratio, and have in vivo antitumor activity similar to that of complexes whose leaving groups have 5–6 carbons. However, increasing DMPG content in liposomal formulations of these complexes having leaving groups with 7–12 carbons results in increased degradation. Complexes with R groups having more than 12 carbons show significant degradation in liposomal formulations, whether the relative DMPG content is low or high.

This inverse correlation between the number of carbons in the R group and the stability within the lipid bilayers was completely unpredictable based on the previous research in this field.

The complexes and formulations of the present invention meet standard stability criteria for pharmaceutical products. They should be useful for treatment of certain disseminated human malignancies, more specifically those known to be sensitive to platinum therapy and that involve the organs that are the natural target of multilamellar liposomes, such as the liver, spleen, bone marrow, and body cavities. They should also be useful for treatment of disseminated human malignancies that are resistant to cisplatin or carboplatin.

DETAILED DESCRIPTION OF SPECIFIC EMBODIMENTS

DACH platinum complexes having leaving groups (R) which are alkyl carboxylato groups were prepared as follows.

Cis, trans-DACH, and trans-dl-DACH were obtained from Turner Labs (The Woodlands, Tex.); trans-l-DACH was purchased from Toray Industries (Tokyo, Japan); and pentanoic, hexanoic, heptanoic, octanoic, nonanoic, decanoic, unidecanoic, lauric, tridecanoic, myristic, pentadecanoic, palmitic, heptadecanoic, and stearic acids were purchased from Aldrich Chemical Co. (Milwaukee, Wis.). $K_2PtCl_4$ was purchased from Aesar (Seabrook, N.H.). All chemicals obtained from commercial sources were used as supplied.

Thin-layer chromatography was performed on pre-coated silica gel plates in a solvent system consisting of methanol-ethyl acetate (1:9). The plates were visualized as yellow spots after exposure to iodine vapor. Nuclear magnetic resonance (NMR) spectra were recorded at 43.055 MHz on an IBM BR200/AF spectrometer by using a 10-mm tunable probe. The $^{195}Pt$ spectra (43.055 MHz) were typically run at a 166,000-Hz spectral width with 100,000 scans, 4 k data points, and 0.012-sec between 10-sec pulses (90° tilt). $^{195}Pt$ chemical shifts were collected in $CHCl_3$ solution (about 30 mmol) at room temperature and were measured relative to an external standard of 2.2M $Na_2PtCl_6$ in $D_2O$ at (0.0) ppm. $^{13}C\{^1H\}$ NMR spectra were measured in $CDCl_3$ solution, with the carbon-13 chemical shifts referenced to the $CDCl_3$ peak at 77.0 ppm. Infrared spectra (4000-250 $cm^{-1}$) were recorded as a KBr pellet using a Beckman 250 MX spectrophotometer.

Preparation of Silver Salts

Silver salts were prepared by mixing silver nitrate (1.7 g, 0.01 mol in 30 ml of $H_2O$) with 0.01 mol of sodium pentanoate (prepared in situ by mixing 2 ml [0.01 mol] of 5N NaOH and 1.02 ml [0.01 mol] of pentanoic acid in 20 ml $H_2O$). A white precipitate formed immediately, and the reaction mixture stirred for 30 min while protected from light by an aluminum foil covering. The final product was separated by filtration, washed with cold water, and dried in vacuo (yield>90%). Silver salts were stored in a container that was protected from light.

Synthesis of Platinum Complexes

Preparation of (DACH) dipentanoatoplatinum(II) Complexes $(DACH)PtI_2$ was synthesized according to a procedure reported earlier. After $K_2PtCl_4$ (20.76 g, 50 mmol) was dissolved in deionized water (500 ml) and filtered, KI (83 g, 0.5 mol in 50 ml of water) was added. The reaction mixture was stirred for 5 min. DACH (5.7 g, 50 mmol) was then added; stirring continued for 30 min. The final product was separated by filtration, washed with a small amount of dimethylformamide, and then washed successively with water, ethanol, and acetone. The $(DACH)PtI_2$ complex (1.4 g, 2.5 mmol) was suspended in chloroform (100 ml), and 1.013 g (4.85 mmol, 1.95 eq) of silver pentanoate was added as a solid. The reaction mixture was stirred for 24 hours while protected from light and filtered through a fine-mesh sintered glass funnel, which was packed with celite to remove silver iodide. The filtrate was evaporated to dryness under reduced pressure, yielding a yellow solid. The crude product was recrystallized from acetone to give a white product (yield: 75%).

$(DACH)PtR_2$ complexes 2–14 (Table 1) were prepared in a similar manner.

TABLE 1

Elemental analysis of hydrophobic platinum(II) complexes

| Complex No. | Complex Name | Observed (Calculated) % C | % H | % N |
| --- | --- | --- | --- | --- |
| 1 | Cis-trans-dl-DACH*-dipentanoato-platinum(II) | 36.39 (36.28) | 6.50 (6.48) | 5.22 (5.29) |
| 2 | Cis-trans-dl-DACH-dihexanoato-platinum(II).$H_2O$ | 38.30 (38.78) | 6.01 (6.82) | 5.98 (5.02) |
| 3 | Cis,trans-dl-DACH-diheptadecanoatoplatinum(II) | 40.35 (41.02) | 7.20 (7.17) | 5.00 (4.78) |
| 4 | Cis,trans-dl-DACH-dioctanoato-platinum(II) | 43.00 (43.06) | 7.58 (7.50) | 4.76 (4.56) |
| 5 | Trans-dl-DACH-dinonanoato-platinum(II) | 45.01 (44.92) | 7.89 (7.80) | 4.56 (4.36) |
| 6 | Trans-l-DACH-didecanoato-platinum(II) | 47.63 (47.92) | 8.01 (7.99) | 4.19 (4.30) |
| 7 | Trans-l-DACH-bis(unidecanoato)-platinum(II) | 50.39 (49.48) | 8.53 (8.24) | 3.87 (4.12) |
| 8 | Trans-l-DACH-dilauratoplatinum(II) | 50.40 (50.91) | 8.93 (8.48) | 3.79 (3.96) |
| 9 | Trans-l-DACH-bis(tridecanoato)-platinum(II).$H_2O$ | 50.10 (50.99) | 8.78 (8.76) | 3.69 (3.72) |
| 10 | Trans-l-DACH-dimyristato-platinum(II).$H_2O$ | 53.24 (53.47) | 9.10 (8.91) | 3.45 (3.67) |
| 11 | Trans-l-DACH-bis(pentadecanoato)-platinum(II).$H_2O$ | 53.08 (53.39) | 9.38 (9.14) | 3.45 (3.46) |
| 12 | Trans-l-DACH-dipalmitatoplatinum(II) | 54.00 (54.47) | 9.47 (9.32) | 3.33 (3.34) |
| 13 | Cis,trans-dl-DACH-bis-heptadecanoatoplatinum(II) | 57.40 (56.67) | 9.95 (9.44) | 2.98 (3.30) |
| 14 | Trans-l-DACH-distearato-distearatoplatinum(II) | 57.52 (57.46) | 9.44 (9.57) | 2.81 (3.19) |

*DACH = 1,2-diaminocyclohexane

All liposomal-platinum preparations were obtained by hydration of previously prepared lyophilized mixtures of the compounds and the lipids.

DMPC and DMPG were obtained from Avanti Polar Lipids (Pelham, Al.). Mixtures of lipids in chloroform were initially prepared and the chloroform was evaporated in a rotary evaporator under vacuum. To the dried lipid film, the platinum compound dissolved in t-butyl alcohol was added. The t-butyl alcohol was removed by lyophilization. A white powder was obtained.

To form the liposome suspension, the lyophilized powder was reconstituted by adding 1 ml 0.9% NaCl solution in water per mg of platinum compound and mild hand-shaking for 2–5 minutes. The liposome suspensions obtained with this technique are multilamellar vesicles of 1 to 5 μm in diameter.

EXAMPLE 1

Platinum complexes having leaving groups with 5–10, 12, 14, and 18 carbons were tested for stability in liposomes. The complexes were formulated in liposomes comprising DMPC:DMPG in 7:3 and 3:7 molar ratios. The extent of the degradation of the complexes was determined by HPLC at 0, 2, and 6 hours after preparation of the liposome formulations. The results are shown in Table 2.

TABLE 2
STABILITY OF LIPOSOMAL FORMULATIONS OF PLATINUM COMPOUNDS
General structure: DACH-Pt-$R_2$
where R is an alkyl-carboxylato group of 5 to 18 carbons

| No. Carbons R | Molar Ratio DMPC:DMPG | Stability* % | | |
|---|---|---|---|---|
| | | 0H | 2H | 6H |
| 5 | 7:3 | 100 | 100 | 100 |
| | 3:7 | 100 | 100 | 100 |
| 6 | 7:3 | 100 | 100 | 100 |
| | 3:7 | 100 | 100 | 100 |
| 7 | 7:3 | 100 | 100 | 100 |
| | 3:7 | 100 | 100 | 92 |
| 8 | 7:3 | 100 | 96 | 96 |
| | 3:7 | 100 | 93 | 78 |
| 9 | 7:3 | 100 | 93 | 93 |
| | 3:7 | 100 | 93 | 79 |
| 10 | 7:3 | 100 | 96 | 96 |
| | 3:7 | 100 | 91 | 79 |
| 12 | 7:3 | 100 | 95 | 95 |
| | 3:7 | 100 | 89 | 79 |
| 14 | 7:3 | 100 | 78 | 67 |
| | 3:7 | 83 | 38 | 35 |
| 18 | 7:3 | 100 | 67 | 52 |
| | 3:7 | 56 | 29 | 28 |

*Determined by HPLC at different time points after preparation of liposome suspensions.

EXAMPLE 2

Platinum complexes having leaving groups with 6, 10, and 14 carbons were tested for efficiency of entrapment in liposomes. As before, the complexes were formulated in vesicles comprising DMPC:DMPG in 7:3 and 3:7 molar ratios. Entrapment efficiency was determined at 0 and 6 hours after entrapment. The entrapment efficiency was determined by measuring the amount of elemental platinum by Atomic Absorption Spectrophotometry bound to the liposome phase after centrifugation at 20,000×g for 45 min. The percent entrapment efficiency is calculated as:

$$\frac{\text{drug bound to lipid phase}}{\text{total initial drug}} \times 100$$

The results are shown in Table 3.

TABLE 3
ENTRAPMENT EFFICIENCY OF DIFFERENT LIPOPHILIC PLATINUM COMPOUNDS IN MULTILAMILLAR LIPOSOMES

| No. CARBONS R | MOLAR RATIO DMPC:DMPG | ENTRAPMENT EFFICIENCY % | |
|---|---|---|---|
| | | 0H | 6H |
| 6 | 7:3 | 96 | 95 |
| | 3:7 | 95 | 95 |
| 10 | 7:3 | 93 | 92 |
| | 3:7 | 92 | 87 |
| 14 | 7:3 | 94 | 82 |
| | 3:7 | 94 | 81 |

EXAMPLE 3

Liposomal formulations of complexes having leaving groups with 6, 10, and 14 carbons were tested in comparison to cisplatin for in vivo antitumor activity against L1210 leukemia. $BDF_1$ mice were inoculated on day 0 with $1 \times 10^6$ L1210 cells intraperitoneally. Treatment was given intraperitoneally on day 1 only. Results were expressed as % T/C. The results are shown in Table 4.

TABLE 4
ANTITUMOR ACTIVITY OF LIPOSOMAL FORMULATIONS OF PLATINUM COMPOUNDS AGAINST L1210 LEUKEMIA

| NO. CARBONS R | DOSE (mg/kg) | % T/C | |
|---|---|---|---|
| | | PC:PG 7:3 | PC:PG 3:7 |
| 6 | 25 | 128 | 128 |
| | 50 | 142 | 157 |
| | 100 | 171 | 185 |
| 10 | 25 | 142 | — |
| | 50 | 171 | 171 |
| | 100 | 200 | 185 |
| 14 | 25 | 150 | 162 |
| | 50 | 162 | 162 |
| | 100 | 175 | toxic |
| cisplatin | 10 | 157 | |
| | | 147 | |
| | | 150 | |

(% T/C = median survival time of treated animals/median survival time of control animals × 100)

The above-described experiments indicate that complexes with leaving groups having 5 or 6 carbon atoms are completely stable (stability at 6 hours 100%) when entrapped within the lipid bilayers, independently of the presence of DMPG. The entrapment efficiency of these complexes is very high (>90%). Further, the in vivo antitumor activity of liposomal formulations of these complexes is similar to or greater than that of cisplatin. Also, these complexes are not isomeric mixtures, and are capable of meeting standard stability criteria for pharmaceutical products.

Complexes of the present invention having leaving groups with 7–12 carbons are very stable (≧95% at 6 hours) in liposomes composed of DMPC:DMPG at a 7:3 molar ratio. The in vivo antitumor activity of these formulations is similar to that of complexes having leaving groups with 5–6 carbons. However, when liposomes with a higher relative content of DMPG (such as DMPC:DMPG 3:7 molar ratio) are used, these complex show significant degradation (stability at 6 hours 79–91%). The stability of this preparation can be optimized by changing the pH of the aqueous solution used for reconstruction.

Complexes of the present invention having leaving groups with more than 12 carbons show significant degradation in liposomal formulation whether the relative DMPG content is low or high.

Methods in accordance with the present invention comprise administering to a mammal an effective amount of the complexes described above. The administering step can suitably be parenteral and by intravenous, intraarterial, intramuscular, intralymphatic, intraperitoneal, subcutaneous, intrapleural, or intrathecal injection, or by topical application or oral dosage. Such administration is preferably repeated on a timed schedule until tumor regression or disappearance has been achieved, and may be used in conjunction with other forms of tumor therapy such as surgery or chemotherapy with different agents. The dose administered of a complex in accordance with the present invention can be between about 5 and about 20 mg/kg of body weight of the human subject to which it is administered.

The description and examples given in this patent are intended to illustrate the present invention. They are not intended to be a complete list of all possible specific embodiments of the present invention. Those skilled in this field will recognize that modifications could be made to the specific embodiments listed here which would still be within the scope of the present invention.

We claim:

1. A complex having the structure $$DACH-Pt-R_2$$

where DACH is diaminocyclohexane, and where each R group is independently a linear alkyl carboxylato group having from about 5 to about 18 carbon atoms.

2. The complex of claim 1, where each R group has from 5-12 carbon atoms.

3. The complex of claim 1, where each R group has from 5-6 carbon atoms.

4. An antitumor composition which includes (a) an amount effective to inhibit tumor growth of a complex having the structure $$DACH-Pt-R_2$$

where DACH is diaminocyclohexane, and where each R group is independently a linear alkyl carboxylato group having from about 5 to about 18 carbon atoms, and (b) at least one phospholipid in the form of a liposome;

where the complex is entrapped within the liposome.

5. The composition of claim 4, where each R group has from 5-12 carbon atoms.

6. The composition claim 5, where each R group has from 5-6 carbon atoms.

7. The composition of claim 5, where the liposome comprises dimyristoyl phosphatidyl choline and dimyristoyl phosphatidyl glycerol.

8. A method of inhibiting tumor growth, including the step of administering to a mammal an amount effective to inhibit tumor growth of a composition which includes (a) a complex having the structure $$DACH-Pt-R_2$$

where DACH is diaminocyclohexane, and where each R group is independently a linear alkyl carboxylato group having from about 5 to about 18 carbon atoms, and (b) at least one phospholipid in the form of a liposome; where the complex is entrapped in the liposome.

9. The method of claim 8, where the complex is entrapped in a liposome comprising dimyristoyl phosphatidyl choline and dimyristoyl phosphatidyl glycerol.

10. The method of claim 8, where each R group has from 5-12 carbon atoms.

11. The method of claim 8, where each R group has from 5-6 carbon atoms.

* * * * *